United States Patent [19]

Freeland

[11] Patent Number: 4,990,147
[45] Date of Patent: Feb. 5, 1991

[54] ABSORBENT ARTICLE WITH ELASTIC LINER FOR WASTE MATERIAL ISOLATION

[75] Inventor: M. Elaine Freeland, Norwood, Ohio

[73] Assignee: The Procter & Gamble Company, Cincinnati, Ohio

[21] Appl. No.: 241,165

[22] Filed: Sep. 2, 1988

[51] Int. Cl.$^5$ ............................................. A61F 13/16
[52] U.S. Cl. .................................. 604/385.2; 604/393
[58] Field of Search ............... 604/347, 397, 396, 392, 604/393, 366, 348, 385.1, 384, 389.2

[56] References Cited

U.S. PATENT DOCUMENTS

| | | |
|---|---|---|
| 2,004,088 | 1/1932 | Alsop . |
| 2,532,029 | 11/1950 | Medoff ............................ 128/287 |
| 3,665,920 | 5/1972 | Davis ............................... 128/287 |
| 4,285,342 | 8/1981 | Mesek ............................. 604/375 |
| 4,655,760 | 4/1987 | Morman et al. .................. 604/385.1 |
| 4,662,877 | 5/1987 | Williams ......................... 604/385 A |
| 4,695,278 | 9/1987 | Lawson .......................... 604/385 A |
| 4,704,116 | 11/1987 | Enloe ............................... 604/385 |
| 4,816,025 | 3/1989 | Foreman ......................... 604/385.2 |
| 4,892,536 | 1/1990 | DesMarais et al. .............. 604/385.2 |
| 4,909,803 | 3/1990 | Aziz et al. ....................... 604/385.2 |

FOREIGN PATENT DOCUMENTS 1520740 8/1978 Japan ............................... 604/385.1

Primary Examiner—C. Fred Rosenbaum
Assistant Examiner—Corrine Maglione
Attorney, Agent, or Firm—Larry L. Huston; John M. Pollaro; Fredrick H. Braun

[57] ABSTRACT

A disposable absorbent article, such as a diaper, having a liquid impervious backsheet, a urine pervious liner, and absorbent core intermediate the backsheet and liner is disclosed. The liner has a passageway to allow communication of solid waste materials to the core, thereby isolating such waste from the skin of the wearer. The liner, is at least partially composed of elastic panels. The elastic panels register the passageway with the anal opening to minimize the size of the passageway and prevent unnecessary exposure of the skin to the solid waste materials.

8 Claims, 3 Drawing Sheets

ABSORBENT ARTICLE WITH ELASTIC LINER FOR WASTE MATERIAL ISOLATION

TECHNICAL FIELD

The present invention relates to disposable absorbent articles, and more particularly to disposable absorbent articles having a lining to isolate fecal material from the skin of the wearer.

BACKGROUND OF THE INVENTION

Several attempts within the art relating to disposable absorbent articles have been made to isolate fecal waste from the wearer. Fecal material which reposes against the skin is often a source of epidermal irritation and makes cleaning of the wearer more difficult.

One attempt is given by U.S. Pat. No. 2,690,749 issued to Nelson, Oct. 5, 1954, which discloses a diaper having separate recesses to accept urine and solid fecal matter. U.S. Pat. No. 2,004,088 issued to Alsop, June 11, 1935 discloses an absorbent pad having a large opening. However, neither reference teaches a means of preventing solid waste materials from contacting the skin of the wearer.

U.S. Pat. No. 3,532,093 issued to Lovret, Oct. 6, 1970, discloses a diaper having separate compartments for the collection of urine and fecal matter. However, this diaper does not have an absorbent core and would therefore be somewhat uncomfortable to the wearer.

An attempt to overcome these problems is disclosed in U.S. Pat. No. 4,662,877 issued to Williams, May 5, 1987, which discloses a diaper having an inelastic urine impervious facing sheet with an aperture to allow waste materials to pass through the facing sheet into the absorbent portion of the diaper. Williams teaches applying longitudinally oriented elastic strands on either side of the aperture.

SUMMARY OF THE INVENTION

It is an object of this invention to obviate the aforementioned problems related to fecal material reposing against the skin of the wearer of a disposable absorbent article.

The invention comprises a disposable absorbent article having a longitudinal axis. A liquid impervious backsheet forms a chassis to hold the other components of the article. Disposed on the backsheet is an absorbent core. Overlying the core is an elastic liner which is generally adjacent the skin of the wearer when the article is in use. The liner has a passageway to allow communication of waste materials to a void space interposed between the liner and core. The liner may be biaxially or uniaxially elastic, with a principal axis of elastic contraction preferably aligned with the longitudinal axis of the absorbent article.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings wherein like parts are given the same reference numerals.

DETAILED DESCRIPTION OF THE INVENTION

A disposable article made according to the present invention is typically a diaper, but could also be a catamenial pad, a product for incontinent adults or any other execution known to those skilled in the art. The disposable article disclosed herein can be manufactured and prepared using methods and materials well known in commercial practice.

The diaper described herein is suitable for infants of either sex weighing from approximately 5 kg. to approximately 11 kg. It is contemplated that various sizes of wearers will be able to use the diaper of this invention, providing it is properly scaled to the size of the wearer.

Figure 1:
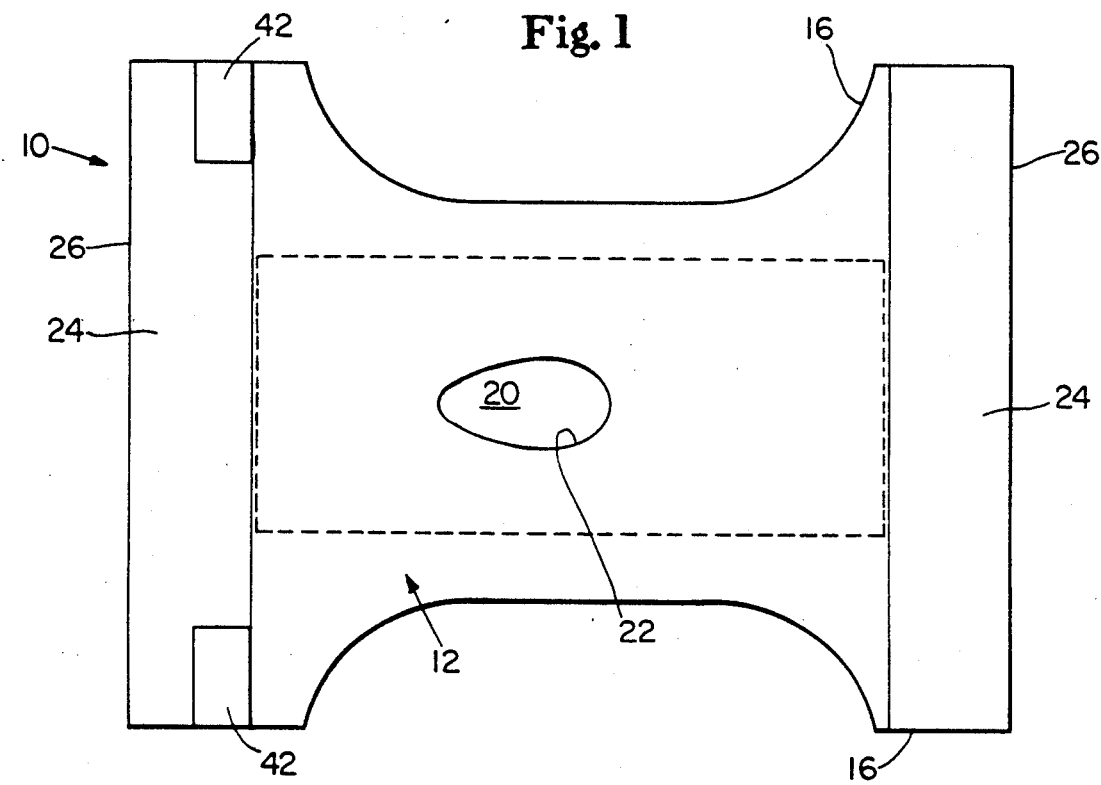
FIG. 1 is a top plan view of a first embodiment of a disposable diaper made according to the present invention and having a liner which is entirely made of an urine pervious elastic material, the core being shown in phantom.

FIG. 1 is a top plan view of an unfolded and flattened diaper 10 having the basic components typical of such an absorbent article comprising an elastic liner 12, a backsheet 14 and absorbent core 18.

The diaper 10 comprises a laminated structure having a generally hourglass shape in the flat, unfolded position. The diaper 10 is generally symmetric about a longitudinal axis oriented from the front to back of the diaper 10, which axis is generally aligned with the machine direction of the diaper 10 during manufacture. A transverse axis is orthogonal to the longitudinal axis of the diaper 10, and intersects the longitudinal axis at or near the midpoint of the diaper 10. As used herein, the front and rear portions of the diaper 10 are defined by and coterminous of the transverse axis and are generally the portions of the diaper 10 disposed to the front and rear of the diaper 10 as observed by the wearer.

The diaper 10 comprises a backsheet 14 which is preferably urine impervious and flexible. An opaque polymer sheet is often utilized. The backsheet 14 provides a chassis for assembly of the diaper 10 about the arcuate posterior of the wearer and which holds the other diaper components hereinafter discussed.

The backsheet 14 is sized to be drawn between the legs of the wearer and fastened about the waist using tapes 42 disposed at the back of the backsheet 14. A diaper 10 generally constructed according to the teachings of U.S. Pat. No. 3,860,003, issued to Buell, Jan. 14, 1975, and incorporated herein by reference is suitable.

A low density polyethylene sheet about 0.01 mm. to about 0.3 mm. thick is typical, with a thickness of about 0.03 mm. being preferred. A backsheet 14 having a longitudinal dimension of about 45 cm., a transverse dimension between either end of the longitudinal edges 16 of about 32 cm. and a transverse dimension at the center of the longitudinal edges 16 of about 20 cm. is suitable.

Juxtaposed with the backsheet 14, towards the skin of the wearer, is a urine absorbent core 18, which is generally soft, conformable and compliant. The core 18 comprises any urine absorbent material such as cellulose fibers, and is typically comminuted cellulosic fiber, often known as air felt. The core 18 may be elasticized or padded and further comprise absorbent gelling polyacrylate materials to increase the core capacity.

The core 18 is designed to absorb and retain the expected volume of liquid discharge for the article's intended use, wear time and capacity. For the embodiment described herein, the core 18 should preferably have a minimum capacity of about 300 ml., to accommodate urine discharges of the wearer.

The core 18 may be generally rectangular, having two opposed faces about 35 cm. to about 40 cm. long and about 10 cm. to about 15 cm. wide, although it will be apparent to one skilled in the art that other shapes or sizes could be used as well. The core 18 is longitudinally shorter than the backsheet 14 to provide a free margin 24 at each transverse edge 26 of the diaper 10.

The core 18 may be integrally affixed to the backsheet 14, may be peripherally affixed to the backsheet 14, or not affixed to the backsheet 14. If it is desired to affix the core 18 to the backsheet 14, affixing may be accomplished with any suitable FDA approved adhesive, such as Century 5227 made by Century Adhesives of Columbus, Ohio.

It is preferable that the core 18 remain intact, in position and not clump, break up or experience undue variations in thickness, otherwise discomfort to the wearer and uneven absorption capacity might result. To provide stability to the core 18, and prevent such disturbances to core 18 uniformity from occurring, the core 18 may be tightly covered with an envelope 20. The envelope 20 may cover either or both faces of the core 18 and be peripherally or integrally affixed to the backsheet 14, using the aforementioned adhesive. The envelope 20 may be made of any urine pervious material, such as spun bonded or carded polyethylene or polypropylene fabric having a caliper of about 0.25 mm. and a basis weight of about 16.7 gm. per sq. m.

Juxtaposed with the absorbent core 18 (or envelope 20, if included), towards the wearer, is a urine pervious, generally nonabsorbent elastic liner 12. The liner 12 is soft and nonirritating to the skin. As used herein, a liner 12 is considered urine pervious if it has a zone or portion of the liner 12 which is specifically adapted to permit urine, but generally not solid fecal material, to pass therethrough, even though a portion or zone of the liner 12 may be urine impervious.

The elastic liner 12 may be made of an elastomeric fiber nonwoven thermoplastic polyurethane elastomer spun bonded fabric or an inelastomeric fiber knitted fabric. If an elastomeric fabric is selected, it preferably does not resemble the feel of natural rubber when placed against the skin. Kanebo fabric made by the Kanebo Company of Osaka, Japan and having a basis weight between about 25 g. and about 35 g. per sq. m. and a thickness between about 0.11 mm. and about 0.21 mm has been found suitable, with a basis weight of about 25 g. per sq. m. being preferred.

If a knitted fabric is selected, nylon as commonly used to manufacture women's stockings is suitable. A fabric of nylon or Antron/Lycra made by the Du Pont Company of Wilmington, Del. and having a basis weight of about 80 g. per sq. m. has been found to work well.

The liner 12 is longitudinally contracted, or foreshortened, to enhance the conformability and shaping of the liner 12 to the buttocks of the wearer. The magnitude of the longitudinal contraction should be great enough to provide a snug fit, and maintain this fit during various motions of and throughout the period worn by the wearer. However, the magnitude of the longitudinal contraction should not be so great as to cause marking or irritation of the wearer's skin.

If the Kanebo fabric is selected, the liner 12 may advantageously have from about 75 to about 100 percent elongation in the uncontracted state and work well in the diaper 10 disclosed above. If the knitted nylon is selected, the liner 12 may advantageously have about 110 percent elongation in the uncontracted state.

As known to one skilled in the art, both elastomeric fiber nonwoven materials and inelastic fiber knitted materials provide elasticity, however achieve it in different manners. Without limiting the invention to any theory of operation, it is known that in the former case elasticity is achieved through the stretching of elastomeric fibers while in the latter case the fibers are knit to achieve elasticity. It is further recognized that either type of material is available with biaxial or uniaxial elasticity. One principal axis of elasticity is preferably oriented generally parallel to the longitudinal axis of the diaper 10.

The liner 12 may generally correspond in size and shape to the backsheet 14. The liner 12 is at least partially, and preferably fully, peripherally affixed to the backsheet 14, laminating the core 18 intermediate the liner 12 and backsheet 14. The liner 12 may be affixed to the backsheet 14 using any well known method such as adhesive affixing, thermal sealing or ultrasonic welding. The liner is considered to be affixed to the backsheet 14 if the liner 12 is directly attached to the backsheet 12 (as shown) or indirectly attached to the backsheet 14 through a separate component.

Associated with the liner 12 is a passageway 22 which permits communication of waste materials, particularly including but not limited to solid fecal materials, through the liner 12 and into the region of the absorbent core 18, thereby isolating the waste materials from the skin of the wearer. In a preferred embodiment, the passageway 22 takes the form of an aperture. As used herein, a passageway is any opening which is sufficient to permit fecal material to pass through the liner 12 without significant obstruction. As used herein the term aperture includes but is not limited to holes, slits and combinations thereof. Preferably the aperture is an oblong hole having a doubly convex shape.

The size of the passageway 22 is a balance between the minimum size necessary to accommodate variations in the placement of the anus relative to the perineum and various cross sections of solid fecal material, while minimizing undue skin contact with the waste material. It is preferred that the passageway 22 have a greater longitudinal than transverse dimension, to ensure registration with the anal opening when the diaper 10 is placed in various longitudinal alignments on the infant.

An aperture having a longitudinal dimension of about 4.0 cm. to about 6.5 cm., and a transverse dimension between about 1.5 cm. and about 6.0 cm. is suitable. The aperture is generally transversely centered on the liner 12 and longitudinally offset at least about 1 cm. towards the back of the diaper 10.

The liner 12 preferably has an inelastic area, referred to as a free margin 24, at each end of the diaper 10 intermediate the transverse edge 26 of the core 18 and the transverse edge 26 of the backsheet 14. This arrangement reduces liner wrinkling and contraction in the free margin 24 areas, providing more comfort to the user and reducing leakage around the waist of the diaper 10. Also, by making the elastically contracted portion of the liner 12 shorter than the backsheet 14, the diaper 10 will bow concave towards the liner 12 when the liner 12 and backsheet 14 are affixed, creating a frame suitable to accommodate the arcuate posterior of the wearer. For a backsheet 14 having a length of about 45 cm., as described above, a liner 12 having a longitudinally elastic portion ranging in longitudinal dimension from about 23 cm. to about 36 cm. is typically suitable.

The longitudinally contracted elastic is at least partially disposed longitudinally nonadjacent the passageway 22. As used herein, longitudinally nonadjacent refers to any portion of the liner 12 which is displaced from the passageway 22 towards either transverse edge 26 of the diaper 10. Alternatively stated, any point on the liner 12 through which a line parallel to the transverse axis can be drawn without intersecting the passageway 22 is longitudinally nonadjacent the passageway 22.

Without being limited to any theory of operation, it is believed this arrangement causes the liner 12 to better conform to the complex curvatures of the buttocks of the wearer and obviates longitudinal collapse of the passageway 22. Furthermore, it is believed this arrangement aligns the passageway 22 to the anal opening of the wearer and provides for affixing of the liner 12 against the skin of the wearer. Preferably, a liner 12 having both front and rear elastic panels, one disposed longitudinally on either side of the passageway 22 (and which may encompass the passageway 22) is provided, although a diaper 10 with either a front or rear elastic panel longitudinally offset from the passageway 22 will provide at least a portion of the aforementioned benefits and is within the scope of the claimed invention.

Figure 2:
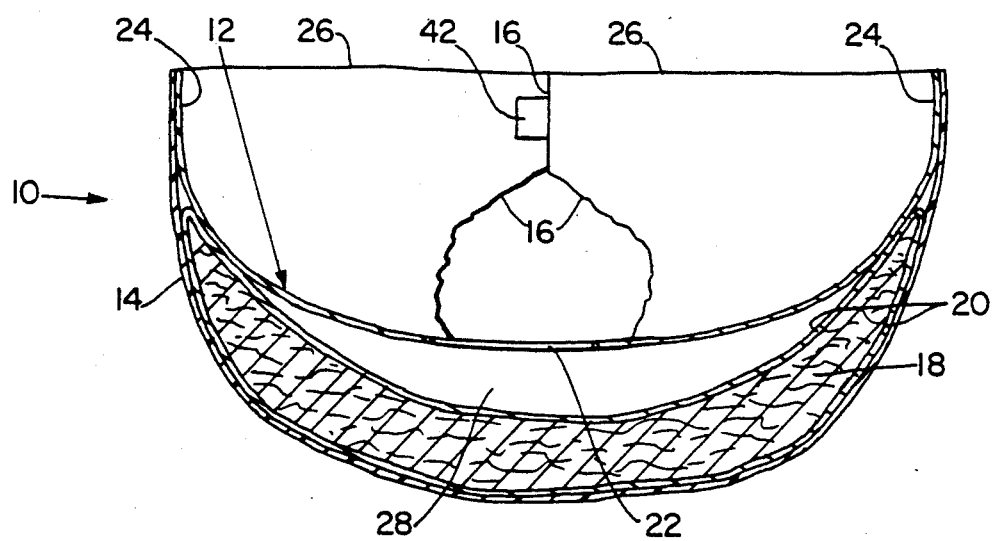
FIG. 2 is a vertical sectional view of the diaper of FIG. 1 when assembled about a wearer in the standing position, not shown, showing the void space between the liner and core.

As shown in FIG. 2, when worn, ideally the longitudinally contracted diaper liner 12 will generally conform to the wearer, while the larger radius of curvature of the absorbent core 18 will allow the core 18 to fall away from the liner 12 and create a void space 28 thereinbetween. Alternatively stated, the differential radii of curvatures creates a shallow hole in the absorbent core 18 to collect waste materials and isolate the collected materials from the wearer, preventing epidermal irritation.

The volume of void space 28 is not critical, so long as at least about 90 gm. of fecal material can be accommodated. Likewise, the void space 28 shape is not critical, and indeed will be irregular. Preferably the liner 12 is not affixed to the core 18 near the vicinity of the passageway 22, otherwise the capacity of void space 28 may be substantially reduced. If desired, the urine acquiring zone of the liner 12 may be adhered to the core 18 to promote urine transmission through the liner 12.

With continuing reference to FIG. 2, in a second embodiment a diaper 10 having an inelastic liner 12 longitudinally shorter than the backsheet 14 is provided. The inelastic liner 12 is longitudinally foreshortened relative to the backsheet 14 and is peripherally affixed to the backsheet 14 at the transverse edges of the liner 12 in accordance with any of the well known affixing methods disclosed above. Preferably the inelastic liner 12 is totally peripherally affixed to the backsheet 14, including both the transverse and longitudinal edges. It will be understood by one skilled in the art that the affixed transverse edges of liner 12 are a longitudinally nonadjacent liner contracting means.

A greater differential in longitudinal dimensions between the liner 12 and backsheet 14 will generally provide a greater void space 28 volume. For the embodiment described herein, the liner 12 is preferentially foreshortened at least about 5 cm. relative to the backsheet 14.

The inelastic liner 12 material is soft, nonirritating to the skin and may be urine pervious or urine impervious. A formed film polyolefinic sheet about 0.01 mm. to about 0.3 mm. thick is suitable. For the embodiment described herein, a formed film polyethylene sheet about 0.03 mm. thick and having about 0 to about 30 percent open area works well.

As discussed with respect to the first embodiment, it is preferred that the liner 12 be sized and positioned to be peripherally attached to the backsheet 14 coterminous of the absorbent core 18, to provide a wrinkle-free and smooth free margin 24. Obviously, the liner 12 and backsheet 14 may be affixed at the longitudinal edges 16 and, similar to the first embodiment, is preferably totally peripherally affixed.

The foreshortened liner 12 of the second embodiment preferably provides the void space 28 intermediate the liner 12 and core 18 and illustrated by FIG. 2. In such an embodiment, due to the absence of elastic means for longitudinally contracting the liner 12 and making it conform somewhat more closely to the skin of the wearer, it is more desirable that a proper and snug fit of the liner 12 be achieved and maintained.

Figure 3:
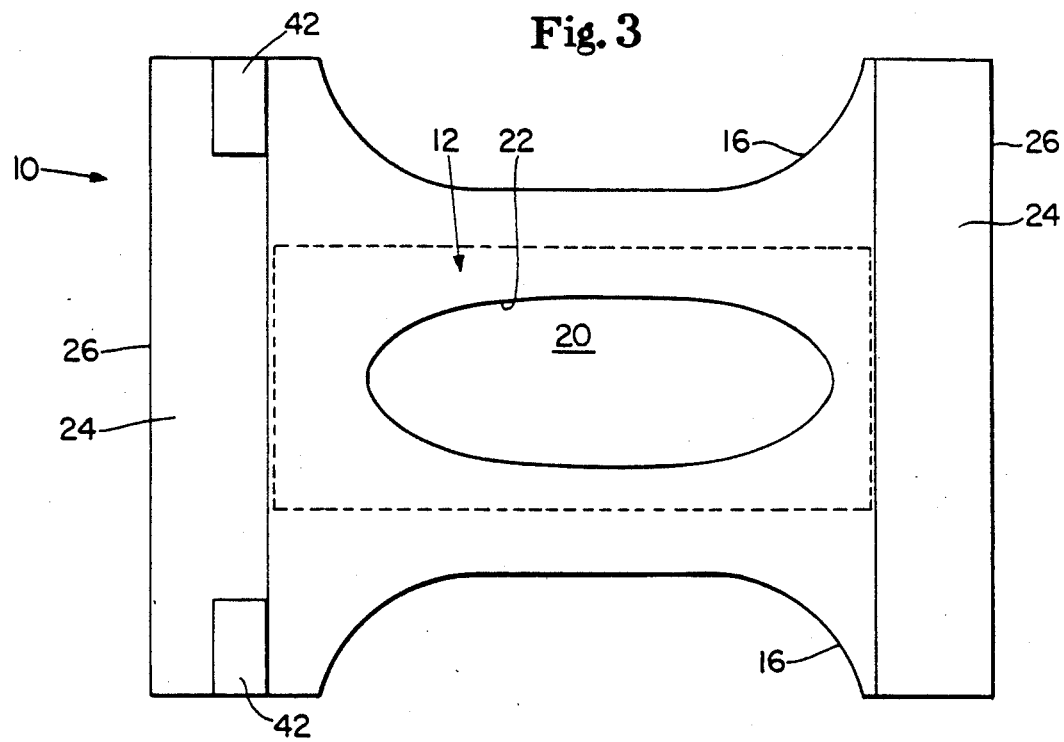
FIG. 3 is a top plan view of a second embodiment of a diaper made according to the present invention having a urine impervious liner, the core being shown in phantom.

In a third embodiment illustrated by FIG. 3, a urine impermeable elastic liner 12 is provided. The liner 12 is preferably made of any such material known in the art and has the characteristics and physical properties described above. One material which works well is the elastic fabric having inelastic fibers disclosed in U.S. Pat. No. 4,107,364, issued to Sissan, Aug. 15, 1978, and incorporated herein by reference. A liner 12 having an elongation of about 25 percent in the uncontracted state works well. Alternatively, a Kanebo fabric liner 12, described above, having a basis weight ranging from about 75 to about 100 g. per sq. m. is urine impervious, and works well with an elongation of about 50 to about 75 percent in the uncontracted state.

To obviate urine from being intercepted and retained against the skin by the liner 12, a larger passageway 22 to accommodate both genitals and permit urine to communicate to the core 18 is provided. For the embodiment described herein, a convexly rectangular aperture having a maximum longitudinal dimension of about 12 cm. to about 23 cm. and a transverse dimension of about 6 cm. to about 10 cm. is suitable, with a longitudinal dimension of about 18 cm. and a transverse dimension of about 8 cm. being preferred. To position the front edge of the passageway 22 outwardly of the genitalia, the hole is longitudinally offset towards the front of diaper 10. A longitudinal offset of about 1.6 cm. towards the front of the diaper 10 works well for the embodiment described herein.

Other variations according to the diapers described above may be advantageously utilized with any of the foregoing embodiments. For example, a urine pervious liner 12 having panels of different materials, including elastic and inelastic panels of the materials described above, may be used.

Figure 4:
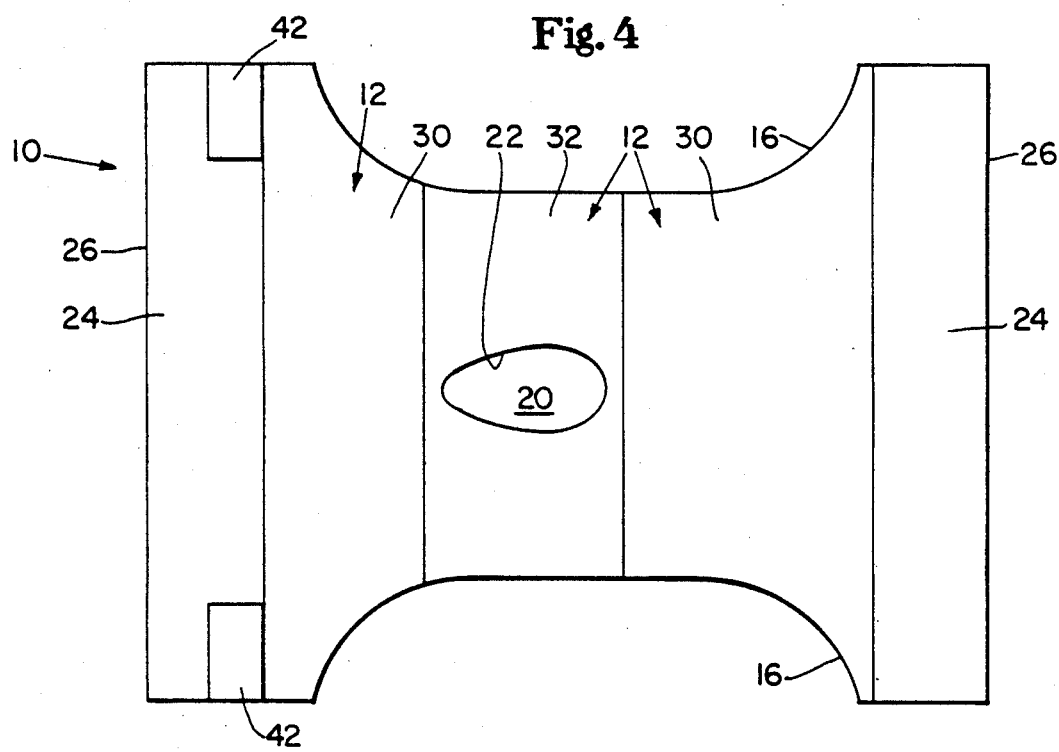
FIG. 4 is a top plan view of a variation of the first embodiment, showing a diaper having a longitudinally centered trisection.
Figure 5:
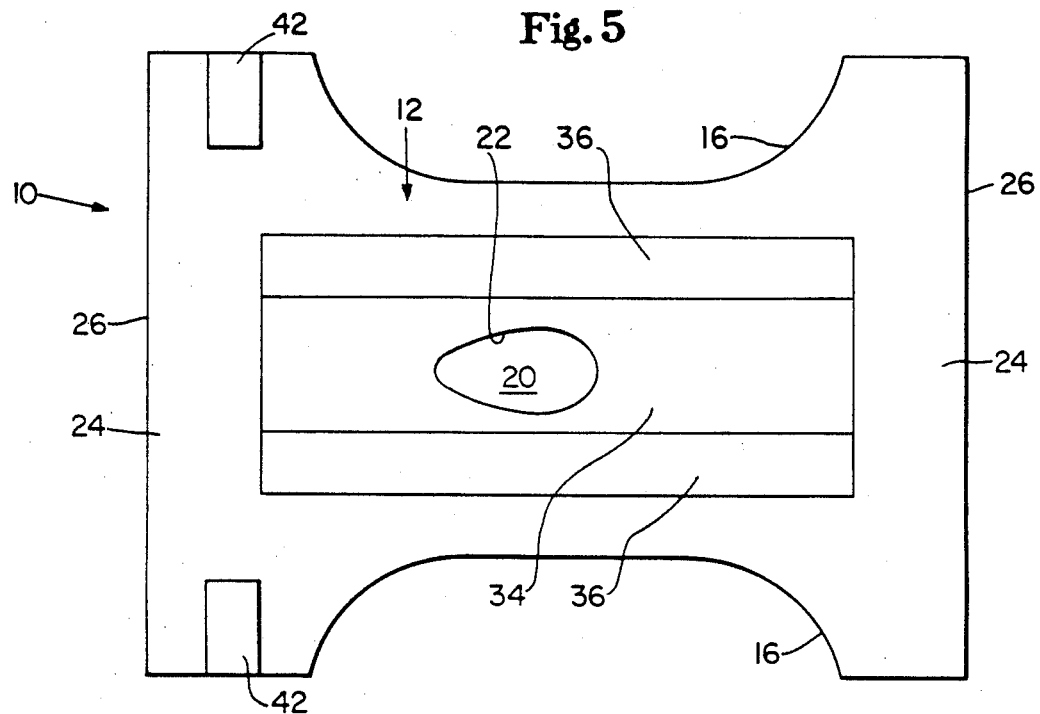
FIG. 5 is a top plan view of another variation of the first embodiment, showing a diaper having a transversely centered trisection.

Specifically, as illustrated in FIG. 4, a liner 12 having front and rear panels 30 made of an elastic material, and a longitudinally centered inelastic trisection 32, intermediate and adjacent the elastic panels 30 and encompassing the passageway 22 may be used. This variant provides the advantage that the inelastic liner panel 32 adjacent the passageway 22 may be somewhat stiffened, as described below, to maintain the passageway 22 in an open condition while the diaper 10 is in use. The elastic panels 30 of such an execution may be limited to the centrally transverse portions of the panels 30, and particularly may coincide with the transverse extent of the passageway 22. It will be apparent to one skilled in the art the materials of the panels 30 and central trisection 32 may be transposed so that the central trisection 32 is made of an elastic material and the panels 30 are made of an inelastic material. However, as shown, for either diaper liner 12 illustrated in FIG. 4 it is not necessary that any one trisection have an area or a length equivalent to those of any other given trisection or be symmetric about either axis. Alternatively, as illustrated in FIG. 5, a liner 12 having a transversely centered elastic trisection 34 with inelastic adjacent side panels 36 may be used. This arrangement provides the advantage, described above, that the passageway 22 is longitudinally strained by the placement of the elastic panel 34. The diaper liner 12 diametrically opposite that shown in FIG. 5 has been found to work well for female infants. Such a liner 12 has a transversely centered inelastic trisection 34 intermediate and adjacent elastic side panels 36. As shown, and described relative to FIG. 4, it is not necessary that any one trisection of either diaper 10 illustrated by FIG. 5 have an area or a length equivalent to those of any other given trisection or be symmetric about either axis.

Figure 6:
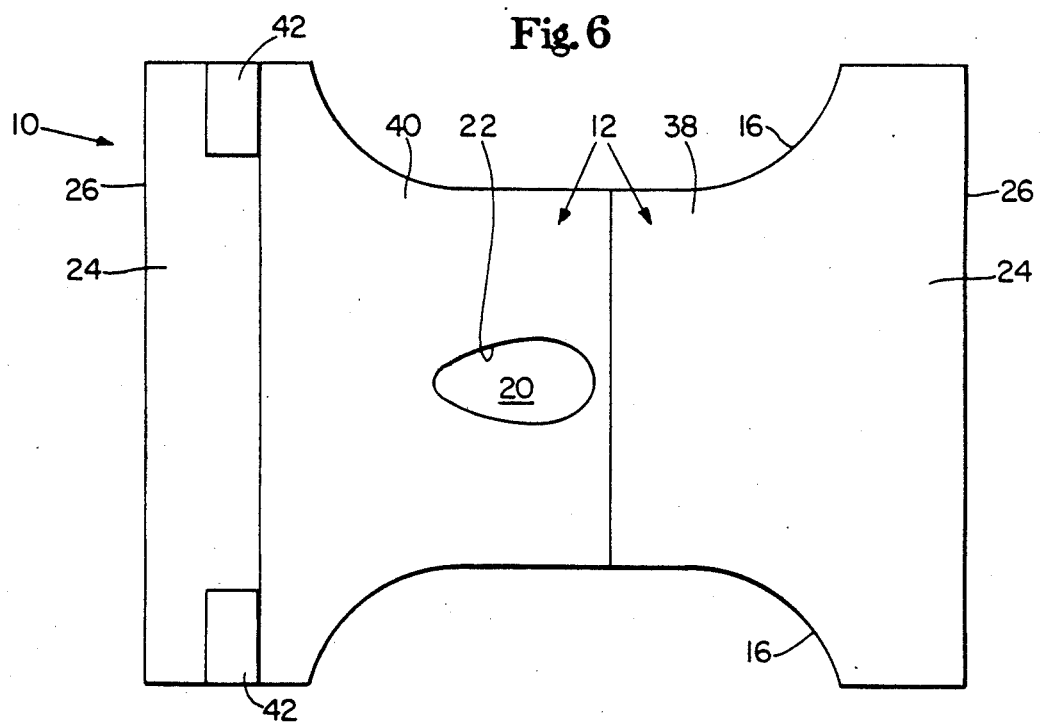
FIG. 6 is a top plan view of yet another variation of the first embodiment, showing a diaper having an elastic panel longitudinally offset from the passageway.

In yet a further alternative illustrated by FIG. 6, a diaper having an elastic front (or rear) panel 40, longitudinally offset from the passageway 22 and which may or may not encompass the passageway 22, and an inelastic rear (or front) panel 38 may be advantageously utilized. Such a variant provides the advantage that the diaper 10 made be made to selectively more closely conform to either the buttocks or genitals of the wearer. All such variations, including those which provide asymmetry about either or both axes, are contemplated to be within the scope of the present invention.

As described above, the elastic and inelastic panels may be joined by any means commonly known to those skilled in the art including adhesive affixing, thermal sealing, and ultrasonic welding. It is preferred that the juncture of the adjacent panels not have a seam which will abrade or irritate the wearer.

It will be apparent to one skilled in the art that other sizes and shapes of passageway 22 apertures are feasible to permit waste materials to pass through the liner 12. For example, a diamond shaped aperture of the aforementioned dimensions and having the corners oriented in the longitudinal and transverse directions is suitable. An aperture such as a slit having a longitudinal dimension ranging about 4.0 cm. to about 6.0 cm. and a transverse dimension of about 0.5 cm. may be used. If the diaper 10 is to be scaled for a larger infant, a larger passageway 22 disposed closer to the rear of the diaper 10 may be desirable. All such passageways 22 are within the scope of the invention.

If desired, the portion of the liner 12 near the passageway 22 may be reinforced to prevent tearing or wrinkling. Reinforcement may be accomplished by providing a double thickness of the liner 12 material in a band adjacent and concentric of the passageway 22 and having a radial dimension of about 1.0 cm. to about 2.0 cm.

Alternatively, the passageway 22 may be elasticized such that it is smaller in size until solid fecal material passes through. Elasticization may be provided by circumscribing the passageway 22 with an elastic strand. As used herein, an elastic strand may be of any cross section and has substantially greater length than transverse dimension. Elastic strands having an untensioned generally rectangular cross section ranging from about 2.4 mm to about 6.4 mm by about 0.2 mm, an elastic modulus of about 125,000 kg. per sq. m. at about 100 to about 200 elongation are suitable. The elastic strands may percent advantageously have about 50 to about 100 percent elongation in the uncontracted state, with higher elongations being generally preferred for holes of greater circumference. Fulflex 9411 strands made by the Fulflex Company of Scotland Neck, N.C. have been found to work well.

If desired, a transverse contracting means may be incorporated into the liner 12 of any embodiment described above, for example by orienting a principal axis of elastic contraction in any nonlongitudinal orientation. This method is feasible for both biaxially elastic and uniaxially elastic materials.

The magnitude of the transverse contraction is not critical, but may be used to generally neutralize any lateral necking which occurs due to the longitudinal contraction. If a knitted nylon fabric having a longitudinal uncontracted elongation of about 110 percent is used, a transverse contraction increasing from about 10 percent at the transverse edges of the liner 12 to about 190 percent at the center of the liner 12 has been found to work well. By increasing the amount of transverse contraction as the center of the diaper 10 is approximated, the passageway 22 may be pulled open and therefore more readily allow solid fecal material to communicate through the liner 12 and enter the void space 28 between the liner 12 and absorbent core 18.

What is claimed is:

1. A disposable absorbent article having a longitudinal axis, said article comprising:
    a urine impervious backsheet;
    an elastic liner made of a two-dimensional elastic material and having at least one passageway through said liner and adapted to permit waste materials to pass through said liner, said liner being at least partially peripherally affixed to and foreshortened relative to said backsheet to form a void space registered with said passageway and intermediate said liner and said backsheet; and
    an absorbent core intermediate said liner and said backsheet.

2. A disposable absorbent article having a longitudinal axis, said article comprising:
    a urine impervious backsheet;
    a liner having at least one passageway through said liner and adapted to permit waste materials to pass through said liner, said liner further having a trisection made of a first material and two panels made of a second material, said trisection being longitudinally centered intermediate said panels, one of said first and said second materials being elastic and made of a two-dimensional elastic material, the other being inelastic, said liner being at least partially peripherally affixed to and foreshortened relative to said backsheet to form a void space registered with said passageway and intermediate said liner and said backsheet; and an absorbent core intermediate said liner and said backsheet.

3. A disposable absorbent article having a longitudinal axis, said article comprising:

a urine impervious backsheet;

a liner having at least one passageway adapted to permit waste materials to pass through said liner, said liner further having a trisection made of a first material and two panels made of a second material, said trisection being transversely centered intermediate said panels, one of said first and said second materials being elastic, the other being inelastic, said liner being at least partially peripherally affixed to said backsheet to form a void space registered with said passageway and intermediate said liner and said backsheet; and an absorbent core intermediate said liner and said backsheet.

4. A disposable absorbent article having a longitudinal axis, said article comprising:

a urine impervious backsheet;

a liner having at least one passageway adapted to permit waste materials to pass through said liner, said liner having a panel disposed longitudinally offset from and to the front of said passageway and made of a first material, said liner further having a panel longitudinally offset from and to the rear of said passageway and made of a second material, one of said first and said second materials being elastic, the other being inelastic, said liner being at least partially peripherally affixed to said backsheet to form a void space registered with said passageway and intermediate said liner and said backsheet; and an absorbent core intermediate said liner and said backsheet.

5. A disposable absorbent article according to claim 1, 2, 3 or 4 wherein said passageway is an aperture.

6. A disposable absorbent article according to claim 5 wherein said passageway has a greater longitudinal dimension than transverse dimension.

7. A disposable absorbent article according to claim 1, 2, 3 or 4 further comprising a means for transverse contraction of said liner.

8. A disposable absorbent article according to claim 7 wherein said means for transverse contraction of said liner comprises an elastic liner panel having a principal axis of elastic contraction oriented in a nonlongitudinal direction.

* * * * *